(12) United States Patent
Hartmann et al.

(10) Patent No.: US 7,588,591 B2
(45) Date of Patent: Sep. 15, 2009

(54) INTERVERTEBRAL IMPLANT

(75) Inventors: Stephan Hartmann, Solothurn (CH); Armin Studer, Langendorf (CH)

(73) Assignee: Synthesis USA, LLC, West Chester, PA (US)

( * ) Notice: Subject to any disclaimer, the term of this patent is extended or adjusted under 35 U.S.C. 154(b) by 112 days.

(21) Appl. No.: 11/414,112

(22) Filed: Apr. 28, 2006

(65) Prior Publication Data

US 2006/0259037 A1 Nov. 16, 2006

Related U.S. Application Data

(63) Continuation of application No. PCT/CH03/00706, filed on Oct. 30, 2003.

(51) Int. Cl.
*A61B 17/70* (2006.01)
*A61F 2/44* (2006.01)

(52) U.S. Cl. .................. 606/249; 606/246; 606/248; 606/250; 623/17.13

(58) Field of Classification Search .............. 623/17.13; 606/246, 248, 249, 250
See application file for complete search history.

(56) References Cited

U.S. PATENT DOCUMENTS

| | | | |
|---|---|---|---|
| 5,059,193 A | 10/1991 | Kuslich | 606/61 |
| 5,084,049 A * | 1/1992 | Asher et al. | 606/61 |
| 5,496,318 A | 3/1996 | Howland et al. | 606/61 |
| 6,235,030 B1 | 5/2001 | Zucherman et al. | 606/61 |
| 6,312,431 B1 | 11/2001 | Asfora | |
| 6,332,882 B1 | 12/2001 | Zucherman et al. | 606/61 |
| 6,332,883 B1 | 12/2001 | Zucherman et al. | 606/61 |
| 6,364,883 B1 | 4/2002 | Santilli | |
| 6,419,676 B1 | 7/2002 | Zucherman et al. | 606/61 |
| 6,451,019 B1 | 9/2002 | Zucherman et al. | 606/61 |
| 6,500,177 B1 | 12/2002 | Martinelli et al. | 606/57 |
| 6,652,527 B2 | 11/2003 | Zucherman et al. | 606/61 |
| 6,669,697 B1 * | 12/2003 | Pisharodi | 606/264 |
| 6,695,842 B2 | 2/2004 | Zucherman et al. | 606/61 |
| 6,699,246 B2 | 3/2004 | Zucherman et al. | 606/61 |
| 6,699,247 B2 | 3/2004 | Zucherman et al. | 606/61 |
| 6,733,534 B2 | 5/2004 | Sherman | 623/17.16 |
| 7,029,473 B2 | 4/2006 | Zucherman et al. | 606/61 |

(Continued)

FOREIGN PATENT DOCUMENTS

GB 780 652 8/1957

(Continued)

*Primary Examiner*—David H Willse
*Assistant Examiner*—Javier G Blanco
(74) *Attorney, Agent, or Firm*—Stroock & Stroock & Lavin LLP

(57) ABSTRACT

An intervertebral implant includes a middle part, comprising two pins, which can be introduced into the intervertebral space between two vertebrae having a central axis, a first end intersecting the central axis, and a second end intersecting the central axis, and two longitudinal parts each with a longitudinal axis extending transversely to the central axis of the middle part and each with an apposition surface directed transversely to the central axis of the middle part contacting the two processi spinosi of two adjacent vertebra bodies. Each part is connectable with one end of the middle part in such a manner that the apposition surfaces are directed against one another. The middle part of the implant is extendable transversely to its central axis along the longitudinal axes of the two parts.

7 Claims, 3 Drawing Sheets

U.S. PATENT DOCUMENTS

| | | | |
|---|---|---|---|
| 7,201,751 B2 | 4/2007 | Zucherman et al. | 606/61 |
| 7,335,203 B2 * | 2/2008 | Winslow et al. | 606/249 |
| 2004/0220568 A1 | 11/2004 | Zucherman et al. | 606/61 |
| 2005/0055031 A1 | 3/2005 | Lim | 606/99 |
| 2005/0143738 A1 | 6/2005 | Zucherman et al. | 606/61 |
| 2005/0203512 A1 | 9/2005 | Hawkins et al. | 606/61 |
| 2005/0203624 A1 | 9/2005 | Serhan et al. | 623/17.11 |
| 2005/0209603 A1 | 9/2005 | Zucherman et al. | 606/90 |
| 2005/0228383 A1 | 10/2005 | Zucherman et al. | 606/61 |
| 2005/0261768 A1 | 11/2005 | Trieu | 623/17.11 |
| 2006/0084988 A1 | 4/2006 | Kim | 606/61 |
| 2006/0085069 A1 | 4/2006 | Kim | 623/17.11 |
| 2006/0085070 A1 | 4/2006 | Kim | 623/17.11 |
| 2006/0184247 A1 | 8/2006 | Edidin et al. | 623/17.11 |
| 2006/0184248 A1 | 8/2006 | Edidin et al. | 623/17.11 |
| 2006/0241601 A1 | 10/2006 | Trautwein et al. | 606/61 |
| 2006/0264938 A1 | 11/2006 | Zucherman et al. | 606/61 |
| 2006/0271049 A1 | 11/2006 | Zucherman et al. | 606/61 |
| 2007/0010813 A1 | 1/2007 | Zucherman et al. | 606/61 |
| 2007/0043361 A1 | 2/2007 | Malandain et al. | 606/61 |
| 2007/0043362 A1 | 2/2007 | Malandain et al. | 606/61 |
| 2007/0043363 A1 | 2/2007 | Malandain et al. | 606/61 |
| 2007/0049934 A1 | 3/2007 | Edidin et al. | 606/61 |
| 2007/0049935 A1 | 3/2007 | Edidin et al. | 606/61 |
| 2007/0055237 A1 | 3/2007 | Edidin et al. | 606/61 |
| 2007/0093830 A1 | 4/2007 | Zucherman et al. | 606/61 |
| 2007/0173832 A1 | 7/2007 | Tebbe et al. | 606/61 |
| 2007/0203493 A1 | 8/2007 | Zucherman et al. | 606/61 |
| 2007/0203497 A1 | 8/2007 | Zucherman et al. | 606/61 |
| 2007/0203501 A1 | 8/2007 | Zucherman et al. | 606/61 |
| 2007/0208347 A1 | 9/2007 | Zucherman et al. | 606/61 |
| 2007/0219552 A1 | 9/2007 | Zucherman et al. | 606/61 |
| 2007/0225706 A1 | 9/2007 | Clark et al. | 606/61 |

FOREIGN PATENT DOCUMENTS

| | | | |
|---|---|---|---|
| GB | 780652 | * | 8/1957 |
| WO | WO 98/46173 | | 10/1998 |
| WO | WO 03/015645 | | 2/2003 |
| WO | WO 2005/009300 | | 2/2005 |
| WO | WO 2006/064356 | | 6/2006 |

* cited by examiner

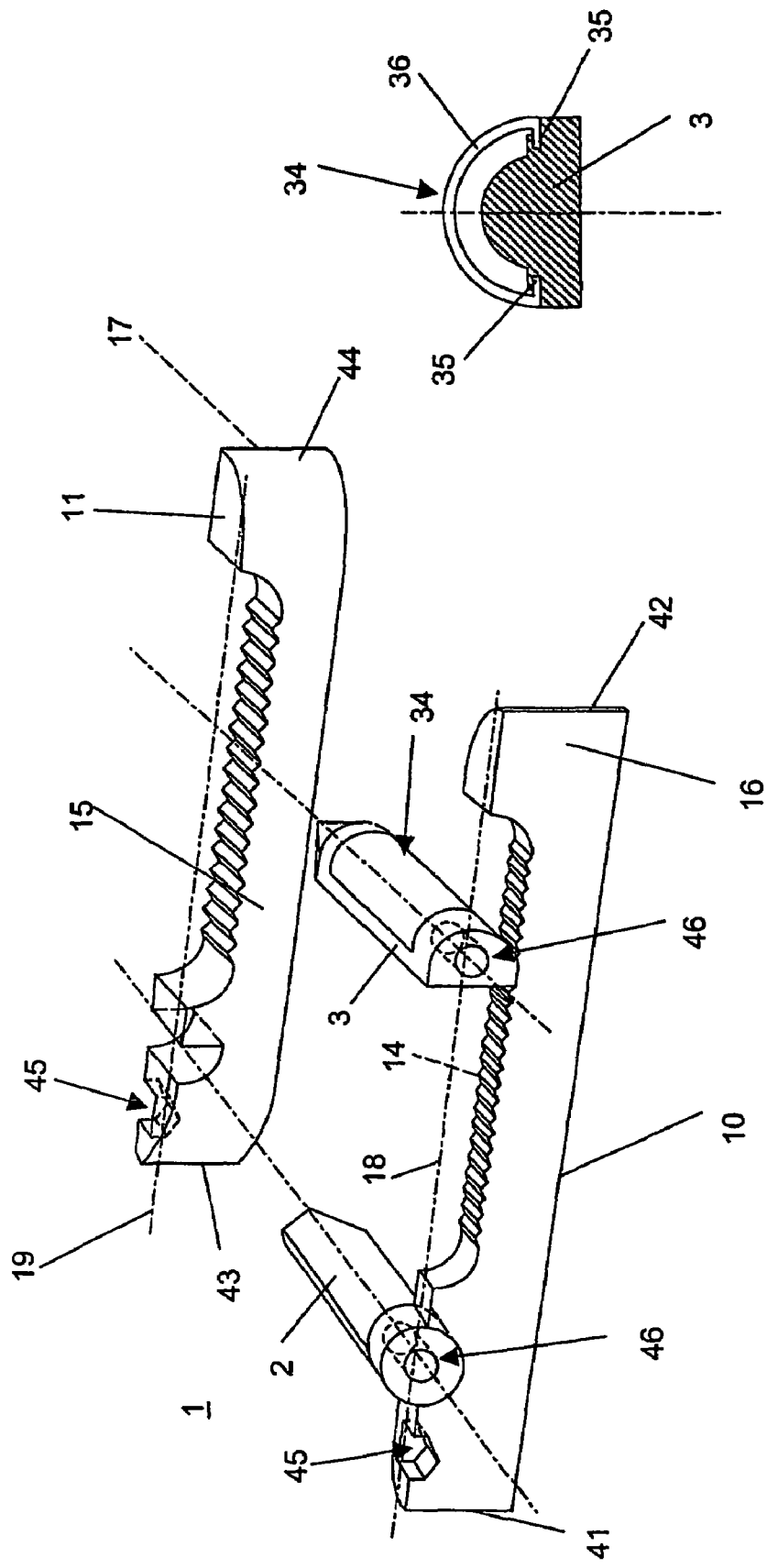

INTERVERTEBRAL IMPLANT

CROSS REFERENCE TO RELATED APPLICATION

This application is a continuation of International Patent Application No. PCT/CH2003/000706, filed Oct. 30, 2003, the entire contents of which is expressly incorporated herein by reference.

TECHNICAL FIELD

The invention relates to intervertebral implants.

BACKGROUND OF THE INVENTION

Intervertebral implants may be used as spacers for two adjacent bodies of vertebrae in the case of a defective intervertebral disk. The distance between the bodies of vertebrae, reduced by the defective intervertebral disc, can be enlarged by such an implant so that the stress on joints is relieved.

A generic, intervertebral prosthesis is known from the International Publication WO 03/015645 to MATHIEU. This known intervertebral prosthesis comprises a middle piece, which is introduced into the intervertebral space and from which a pair of longitudinal appendices protrude cranially and caudally to the right and to the left of the middle piece so that the middle piece can be held in place by means of the appendices between the processi spinosi of two adjacent bodies of vertebrae. This known prosthesis comprises a middle part which cannot be expanded, so that an extended position of the adjacent bodies of the vertebrae cannot be produced by the prosthesis itself.

International Publication WO 98/46173 to SCHÄR discloses a vertebral prosthesis which can be telescoped by means of a ratchet mechanism. However, this prosthesis must be introduced into the intervertebral space making it necessary to remove the defective intervertebral disc.

SUMMARY OF THE INVENTION

The present invention is to provide a remedy for the above-discussed disadvantages. It is an object of the invention to produce an intervertebral implant comprising elements which can be introduced into the intervertebral space, and, at the same time, permit adjoining bodies of the vertebrae to be extended and to be kept extended. The advantages, achieved with the invention, are seen to lie essentially therein that: the intervertebral space does not have to be emptied; it is possible to extend and fix the adjoining bodies of vertebrae in a desired, extended position; it is not necessary to remove ligaments, especially the supraspinal ligament; the extension takes place directly with the implantation; an infinitely variable extension is possible; and only one implant is required.

In a preferred embodiment, the intervertebral implant has a middle part with a central axis, a first end intersecting the central axis, and a second end intersecting the central axis. The intervertebral implant also includes two longitudinal parts, each having a longitudinal axis extending transversely to the central axis of the middle part, and each with an apposition surface directed transversely to the central axis of the middle part for contacting two processi spinosi of two adjacent vertebrae. Each part is connectable with an end of the middle part so that the apposition surfaces are directed against one another, and the middle part may be extended transverse to its central axis along the longitudinal axes of the two parts.

Preferably, the pins are constructed with a semicircular cross-sectional area, which is orthogonal to the longitudinal axis, the flat surfaces being directed against one another. With that, the advantage can be achieved that the ligaments and the surrounding tissue are affected only slightly when the pins are introduced, especially when they are passed through the ligaments.

In a different embodiment, the ends of the two pins can be fixed positively at the two parts, so that any unintentional displacement of the pins after their extension and fixation is prevented.

In yet another embodiment, each of the two parts comprises an elongated hole which extends from its apposition surface to an exterior surface and the long axes of which are parallel to the longitudinal axes of the two parts. The ends of the pins are secured in the elongated holes by the long side walls of the elongated holes to prevent unintentional movement perpendicular to the long axes of the elongated holes.

In a further embodiment, only one pin is displaceable parallel to the longitudinal axes of the two parts in the elongated holes, while the other pin is firmly connected with one of the two parts even before the implantation.

Some suitable dimensions of the different components of the intervertebral implant are:
 preferably, each part has a height H of between about 10 mm and about 30 mm parallel to its longitudinal axis;
 preferably, each of the pins, has a maximum diametric dimension of between about 2 mm and about 5 mm;
 the displaceability of the two pins parallel to the longitudinal axes of the two parts and relative to one another preferably is between about 7 mm and about 15 mm.

In yet another embodiment, each elongated hole, at its side surfaces parallel to the longitudinal axes of the two parts, has a three-dimensional macroscopic structure, which preferably consists of teeth. Preferably, the two parts are produced from titanium and the two pins from a softer material, so that the softer material of the two pins can be pressed into the macroscopic structuring at the side surfaces of the elongated holes, for example, by axially compressing the pins. The pins are deformed plastically, so that a positive connection of the pins in the elongated holes of the two parts can be achieved.

In a different embodiment, at least one of the two pins comprises elastic means which are directed against the processus spinosus of an adjoining vertebra body so that, in the contact region with the adjoining processus spinosus, the pin is elastically deformable transversely to its longitudinal axis. With that, the advantage may be attained that after implanting between the processi spinosi of two adjacent bodies of the vertebrae parallel to the longitudinal axis of the spinal column, the intervertebral implant is elastic within a desired range. Preferably, these elastic means are constructed as a leaf spring, which is disposed peripherally at a pin, the spring deflection being between about 0.1 mm and about 4.0 mm.

In yet another embodiment, the two parts are panel-shaped, so that the space required for the intervertebral implant is as small as possible.

A method of inserting an intervertebral implant into a patient, the implant having a middle part with a central axis comprising two pins, and two longitudinal parts, a first and second part, each having a elongated hole and an opening and each with an apposition surface directed transversely to the central axis of the middle part, includes the following steps. An incision is made and muscle tissue adjacent to processi spinosi is removed. The first part and middle part are assembled by inserting the two pins into the first part which is then connected to a first clamping jaw of a first instrument. The second part is connected with a second clamping jaw of the first instrument. At this point, the intervertebral is implanted such that the pins connected to the first part are positioned ventrally. The pins are pushed by the first instrument such that the pins front ends pass through the elongated hole and opening of the second part. The pins are extended parallel to the longitudinal axes of the first and second parts using a second instrument, and the two pins are immobilized to the first and second parts using the first instrument, clamping the elongated holes and the two openings of the first and second part such that the pins are compressed by teeth of the elongated holes.

BRIEF DESCRIPTION OF THE DRAWINGS

The intervertebral implant is explained in even greater detail in the following exemplary drawings. The intervertebral implant may be better understood by reference to the following drawings, wherein like references numerals represent like elements. The drawings are merely exemplary to illustrate the structure, operation and method of use of the intervertebral implant and certain features that may be used singularly or in combination with other features and the invention should not be limited to the embodiments shown.

FIG. 2 shows a perspective section through an embodiment of the intervertebral implant with extended pins.

FIG. 3 shows a cross-section, orthogonal to the central axis, of the second pin of the embodiment of the intervertebral implant shown in FIG. 2.

DESCRIPTION OF THE PREFERRED EMBODIMENTS

Figure 1:
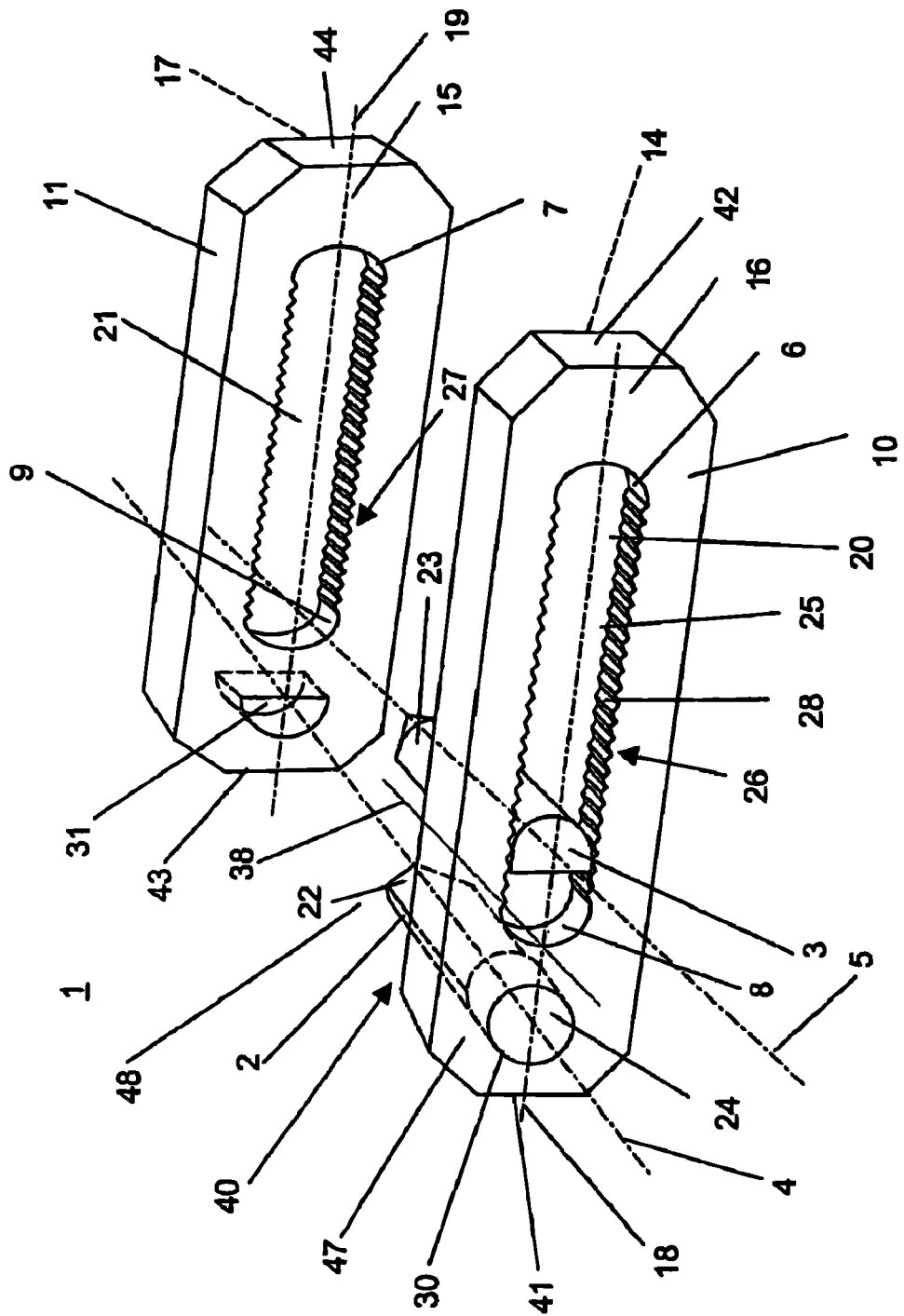
FIG. 1 shows a perspective view of an embodiment of the intervertebral implant with extended pins.
Figure 4:
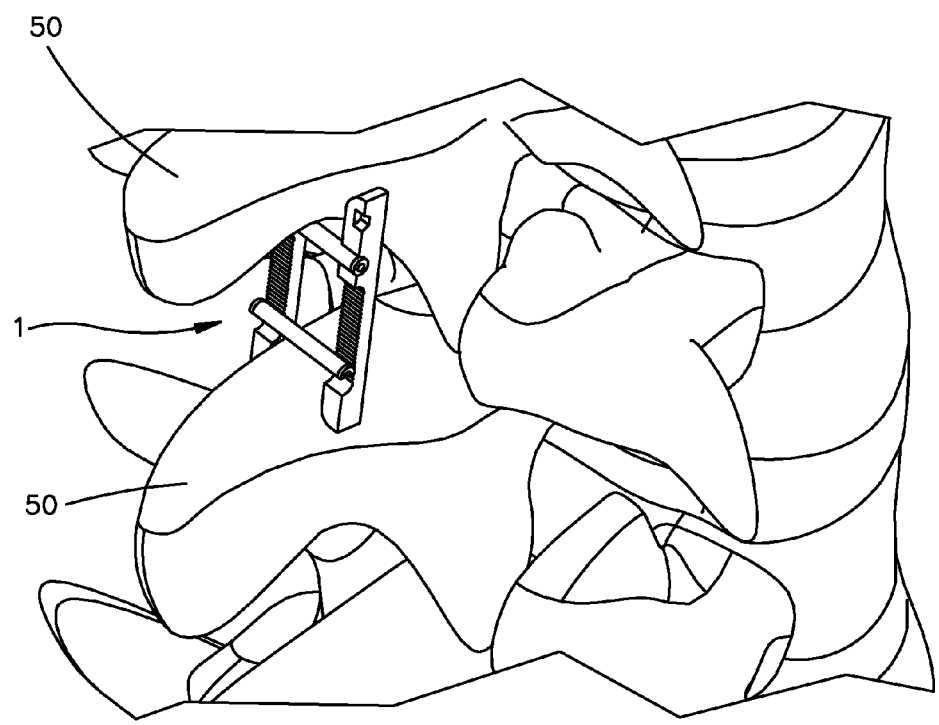
FIG. 4 shows a perspective view of an embodiment of the intervertebral implant between the processi spinosi of two adjacent vertebrae bodies.

An embodiment of the intervertebral implant 1, shown in FIGS. 1 and 4, may comprise essentially two parts 10, 11 which are constructed as panels and each of which has a longitudinal axis 18, 19 and two ends 41, 42, 43, 44 intersecting the longitudinal axes 18, 19. The two parts 10, 11 are disposed parallel to one another and can be immobilized relative to one another by means of a middle part 40. The middle part 40 is disposed between the two parts 10, 11 in such a manner that its central axis 38 extends transversely to the longitudinal axes 18, 19 of the two parts 10, 11 and a part 10, 11 can be fastened to each end 47, 48 of the middle part 40. The two parts 10, 11 each have an apposition surface 14, 15, which is bounded laterally by the two ends 41, 42, 43, 44 and each of which can be brought into contact with one side of the processi spinosi (FIG. 4). Each part 10, 11 has an elongated hole 20, 21 with a long axis parallel to the longitudinal axis 18, 19 of the corresponding part 10, 11. The corresponding elongated holes 20, 21 extend from the apposition surface 14, 15 to the opposite external surface 16, 17. The middle part 40 can be extended parallel to the longitudinal axes 18, 19 of the two parts 10, 11 and is formed by two pins 2, 3, the longitudinal axes 4, 5 of which extend transverse to the apposition surfaces 14, 15. Each of the two elongated holes 20, 21 has a first end 6, 7 intersecting the longitudinal axis 18, 19 of the corresponding part 10, 11 and a second end 8, 9, also intersecting the longitudinal axes 18, 19 of the corresponding part 10, 11. Furthermore, each of the two parts 10, 11 has an opening 30, 31, which is demarcated axially from the elongated holes 20, 21 and of which one opening 30, 31 passes through one of the two parts 10, 11 from the apposition surface 14, 15 to the exterior surface 16, 17. The two openings 30, 31 are disposed coaxially with the longitudinal axis 4 of the first pin 2, so that the rear end 24 of the first pin 2 can be introduced into the first opening 30 and connected firmly with the first part 10 and, during the implantation, may be passed through the second opening 31 in the second part 11 and immobilized. The second pin 3 is passed at the two ends 8, 9 of the elongated holes 20, 21 and may be shifted by means of an extension instrument (not shown) parallel to the longitudinal axes 18, 19 of the two parts 10, 11 in the two elongated holes 20, 21. At the side surfaces 26, 27 of the elongated holes 20, 21, which are parallel to the longitudinal axes 18, 19, three-dimensional macroscopic structures, preferably teeth 28, are disposed, so that the second pin 3 can be immobilized in the elongated holes 20, 21 by axial compression.

The pins 2, 3, having front and rear ends 22, 23, 24, 25, are configured so that they have a cross-sectional surface which is a segment of a circle orthogonal to their longitudinal axis 4, 5. The flat side surfaces of the two pins 2, 3 may be directed against one another and perpendicular to the longitudinal axes 18, 19 of the two parts 10, 11. Moreover, the two pins 2, 3 may be pointed at their front ends 22, 23.

FIG. 2 shows an embodiment of the intervertebral implant 1 which differs from that shown in FIG. 1 only in that the second pin 3 is equipped with elastic means 34. Moreover, the apposition surfaces 14, 15 at the lateral ends 41, 42, 43, 44 of the two parts 10, 11 intersecting the longitudinal axes 18, 19 of the two parts 10, 11 are curved by means for which a better fit of the apposition surfaces 14, 15 to the anatomy can be attained. Preferably these elastic means 34 are constructed as a leaf spring, which is disposed peripherally at a pin, the spring deflection being between about 0.1 mm and about 4.0 mm.

First means 45 for accommodating the tips of an instrument (not shown) penetrating from the direction of the external surfaces 16, 17 are mounted at the first ends 41, 43 of the two parts 10, 11. These first means 45 are constructed here as hexagon sockets for accommodating the instrument tips so that each of the parts 10, 11 are attached to the instrument tip for implantation without shifting or rotating relative to the instrument tip. Second means 46 for accommodating the tips of an instrument (not shown) are mounted at the two pins 2, 3. Second means 46 are constructed here as boreholes penetrating from the rear ends 24, 25 of the two pins 2, 3. The tips of an extension instrument, by means of which the second pin 3 may be shifted parallel to the longitudinal axes 18, 19 of the two parts 10, 11 relative to the first pin 2, may be introduced into these second means 46.

The second pin 3 may comprise at its surface, which adjoins the processus spinosus of a body of a vertebra, elastic means 34, which, after the implantation, enable the processi spinosi at the pins 2, 3 to move relative to one another. As shown in FIG. 3, the elastic means 34 consist essentially of an arc-shaped leaf spring 36 which is clamped between the two apposition surfaces 14, 15 in two radial grooves 36 in the second pin 3 and radially may be deformed elastically. Moreover, the cross-sectional surface of the pin 3, orthogonal to the longitudinal axis 5 of the second pin 3, is reduced in size in the region of the leaf spring 36 so that deflection of the leaf spring 36 becomes possible.

In one embodiment, the ends 22, 23, 24, 25 of the two pins 2, 3 can be fixed positively at the two parts, so that any unintentional displacement of the pins 2, 3 after their extension is prevented.

FIG. 2 shows an embodiment of the intervertebral implant 1 which differs from that shown in FIG. 1 only in that the second pin 3 is equipped with elastic means 34. Moreover, the apposition surfaces 14, 15 at the lateral ends 41, 42, 43, 44 of the two parts 10, 11 intersecting the longitudinal axes 18, 19 of the two parts 10, 11 are curved by means for which a better fit of the apposition surfaces 14, 15 to the anatomy can be attained. Preferably these elastic means 34 are constructed as a leaf spring, which is disposed peripherally at a pin, the spring deflection being between about 0.1 mm and about 4.0 mm.

Some suitable dimensions of the different components of the intervertebral implant 1 are:
- preferably, each part 10, 11 has a height H of between about 10 mm and about 30 mm parallel to its longitudinal axis;
- preferably, each of the pins 2, 3, has a maximum diametric dimension of between about 2 mm and 5 about mm;
- the displaceability of the two pins 2, 3 parallel to the longitudinal axes 18, 19 of the two parts 10, 11 and relative to one another preferably is between about 7 mm and about 15 mm.

Preferably, the two parts 10, 11 are produced from titanium and the two pins 2, 3 from a softer material, so that the softer material of the two pins 2, 3 can be pressed into the macroscopic structuring at the side surfaces of the elongated holes 20, 21, for example, by axially compressing the pins 2, 3. The pins 2, 3 are deformed plastically, so that a positive connection of the pins 2, 3 in the elongated holes 20, 21 of the two parts 10, 11 may be achieved.

In yet another embodiment, the two parts 10, 11 are panel-shaped, so that the space required for the intervertebral implant 1 is as small as possible.

Description of the Implantation Process

A method for implanting the intervertebral implant 1 is now described. After an incision has been made and only the muscles at the sides of the processi spinosi have been removed, the intervertebral implant 1 can be implanted. Because of the pointed configuration of the pins 2, 3 at the front ends 22, 23, removal of the ligaments in the region of the body of the vertebra to be treated is unnecessary for the implantation. The two pins 2, 3 are inserted with their rear ends 24, 25 into the first part 10 and shifted against one another parallel to the longitudinal axis 18 of the first part 10 until they form a middle part 40 with the smallest possible cross-section. The first part 10, together with the two pins 2, 3, is connected with one clamping jaw of an instrument, while the second part 11 is connected with a second clamping jaw of the same instrument. The intervertebral implant 1 is introduced into the vertebral space so that the pins 2, 3 are positioned to the left of the processi spinosi and the ligamenti intervertebrale and the second part 11 is positioned to the right of the processi spinosi. The intervertebral implant is positioned ventrally as far as possible. The pins 2, 3 are pushed by the instrument through the ligaments and passed with the front ends 22, 23 through the elongated hole 21 and the second opening 31 in the second part 11, respectively. Subsequently, the pins 2, 3 are extended parallel to the longitudinal axes 18, 19 of the two parts 10, 11 by means of a second instrument. Because the pins 2, 3 are disposed between adjacent processi spinosi and, during the extension, come to lie in contact with these, the two adjacent bodies of vertebrae are extended by the further extension of the two pins 2, 3. When the desired extension of the two adjacent bodies of vertebrae is attained, the two pins 2, 3 are compressed by pressing the clamping jaws of the instrument together in the elongated holes 20, 21 and the two opening 30, 31 respectively, so that the front and rear ends 23, 25 of the second pin 3 are pressed into the teeth 28 and the pins 2, 3 are connected positively with the two parts 10, 11. After the pins 2, 3 are immobilized in the two parts 10, 11, the instrument can be removed and the incision closed.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An interspinous implant for insertion into an interspinous space located between adjacent first and second vertebral bodies, the implant comprising:

first and second elongated, non threaded pins for insertion into the interspinous space between the spinous processes of said adjacent first and second vertebral bodies, the first elongated pin adapted to contact the spinous process of the first vertebral body, the second elongated pin adapted to contact the spinous process of the second vertebral body, each pin having a longitudinal axis, a first end, and a second end, the first pin being parallel to the second pin; and first and second longitudinal parts, each of the first and second longitudinal parts having a longitudinal axis extending transversely to the longitudinal axis of the first and second pins, and each with an apposition surface directed transversely to the longitudinal axis of the first and second pins for contacting said spinous processes of said two adjacent vertebral bodies, each of the first and second longitudinal parts having a first end and a second end, wherein each longitudinal part is connectable with an end of the first and second pins so that the apposition surfaces are facing toward one another, and wherein each of the first and second longitudinal parts having an opening and an elongated hole, said elongated hole extending generally parallel to the longitudinal axes of the first and second longitudinal parts, respectively, the first and second ends of the first pin being firmly connected within the openings of the first and second longitudinal parts, respectively, so that the first pin is stationary with respect to the first and second longitudinal parts and the first and second ends of the second pin are receivable within the elongated holes of the first and second longitudinal parts, respectively, so that the second pin is movable within the elongated holes formed in the first and second longitudinal parts generally parallel to the longitudinal axis of the first and second longitudinal parts and so that the second pin is moveable with respect to the first pin; and wherein the elongated holes include a plurality of teeth formed on an inner peripheral surface of the elongated holes, said plurality of teeth engaging an outer circumference surface of the first and second ends of the second pin so that the second pin is selectively immobilizable relative to the first and second longitudinal parts, wherein the first end of the first and second pins include a pointed tip, and wherein each of the first and second longitudinal parts are configured in the shape of a panel.

2. The intervertebral implant according to claim 1, wherein each of the pins has a maximum diametric dimension of between about 2 mm and about 5 mm.

3. The intervertebral implant according to claim 1, wherein the second pin can be shifted a distance of between about 7 mm and about 15 mm relative to the first pin parallel to the longitudinal axes of the first and second longitudinal parts.

4. The intervertebral implant according to claim 1, wherein the first and second longitudinal parts are produced from a material which is harder than the material of the first and second pins.

5. The intervertebral-implant according to claim 1, wherein at least one of the first and second pins comprises elastic means so that the pin can be deformed elastically transverse to its longitudinal axis.

6. The intervertebral implant according to claim 5, wherein the elastic means are formed by a leaf spring disposed peripherally.

7. The intervertebral implant-according to claim 5, wherein the elastic means can be deformed elastically by between about 0.1 mm and about 4.0 mm parallel to the longitudinal axes of the first and second longitudinal parts.

\* \* \* \* \*